United States Patent
Paul et al.

[19]

[11] Patent Number: 6,112,121
[45] Date of Patent: Aug. 29, 2000

[54] IMPLANTABLE MEDICAL DEVICE WITH POSITIVE INDICATION OF LEAD CONNECTION AND CONNECTOR THEREFOR

[75] Inventors: Patrick J. Paul; David Prutchi, both of Lake Jackson, Tex.

[73] Assignee: Intermedics Inc., Angleton, Tex.

[21] Appl. No.: 09/150,124

[22] Filed: Sep. 9, 1998

[51] Int. Cl.[7] .................................................. A61N 1/375
[52] U.S. Cl. ................................................. 607/37; 607/36
[58] Field of Search ........................................ 607/36, 37

[56] References Cited

U.S. PATENT DOCUMENTS

| | | |
|---|---|---|
| 4,860,750 | 8/1989 | Frey et al. . |
| 5,443,065 | 8/1995 | Berghoff et al. .................. 128/639 |
| 5,486,202 | 1/1996 | Bradshaw . |
| 5,545,188 | 8/1996 | Bradshaw et al. . |
| 5,626,626 | 5/1997 | Carson .................................. 607/36 |
| 5,645,577 | 7/1997 | Froberg et al. ....................... 607/37 |
| 5,669,790 | 9/1997 | Carson et al. ........................ 607/37 |
| 5,683,433 | 11/1997 | Carson ................................. 607/36 |
| 5,766,042 | 6/1998 | Ries et al. ............................ 439/668 |
| 5,843,141 | 12/1998 | Bischoff et al. ...................... 607/37 |

FOREIGN PATENT DOCUMENTS

| | | | |
|---|---|---|---|
| 0689854 | 1/1996 | European Pat. Off. ......... | A61N 1/08 |
| 98/42408 | 10/1998 | WIPO ............................ | A61N 1/375 |

*Primary Examiner*—Carl H. Layno
*Attorney, Agent, or Firm*—Schwegman, Lundberg, Woessner & Kluth, P.A.

[57] ABSTRACT

An implantable medical device including an enclosure and a header portion attached to the enclosure. The header includes a lead cavity into which a lead can be inserted. The lead cavity includes a compression device, such as a spring, for aligning a highly visible indicator plunger at least partially hidden from view inside the volume defined by an annular electrode, or other opaque object, partially surrounding the lead cavity. The plunger includes at least a portion that is easily visible to a surgeon during implantation of the medical device. When a lead is inserted into the lead cavity, the end of the lead pushes against the indicator plunger thereby moving the plunger and compressing the spring. When the lead is fully inserted into the lead cavity, the plunger becomes visible as it is pushed away from the volume defined by the annular electrode. In this way, the plunger provides a positive indication that the lead has been fully inserted into the header. The annular electrode may also include a retaining surface that will contact a corresponding surface on the plunger should the plunger break loose from the spring. This feature helps to keep the plunger from migrating from the header into the body should the plunger break away from the spring.

25 Claims, 4 Drawing Sheets

IMPLANTABLE MEDICAL DEVICE WITH POSITIVE INDICATION OF LEAD CONNECTION AND CONNECTOR THEREFOR

BACKGROUND OF THE INVENTION

1. Field of the Invention

The present invention generally relates to implantable medical devices. More particular, the invention relates to an implantable device with an improved mechanism for connection of a lead to the implantable device. Still more particularly, the invention relates to an implantable device that provides a positive indication that the lead has been properly connected to the device.

2. Background of the Invention

Many patients require an implantable medical device for any one of a variety of reasons. Many cardiac patients, for example, require an implanted pacemaker or defibrillator to assist the heart to beat properly. Other patients may benefit from an implanted nerve stimulator or drug delivery device. The present invention is described with respect to an implantable cardiac pacemaker, with the understanding, however, that the invention is useful in the context of many other types of implantable devices.

A typical implantable pacemaker generally comprises a hermetically-sealed electronics assembly and one or more flexible "leads" that electrically connect the assembly to the heart. The components of the assembly are enclosed in a housing commonly referred to as the "can." The leads contain electrical conductors that transmit signals generated inside the can to the heart to stimulate the cardiac tissue to beat. One end of the lead (the "proximal" end) mates with the pacemaker header, while the other end (the "distal" end) is routed into an internal chamber of the heart. The distal end of the leads includes one or more electrodes that make direct electrical contact with the tissue of the heart and/or blood within the heart. The leads can be any desired length, but generally are between 18 and 30 inches long. With this configuration, the can, which typically is small enough to fit in one's palm, can be positioned in any convenient location within the chest cavity and not necessarily immediately adjacent the heart. The distal end of the lead is routed along a convenient path, such as through an artery or vein, into one of the four chambers of the heart. Once inside a chamber, an electrode on the distal end of the lead is then attached to the internal lining, or myocardium, of the heart. Then, the can is positioned in the chest cavity and the surgeon connects the lead, or leads, to the can.

One concern that surgeons face when implanting a pacemaker in a patient is ensuring that the lead is properly inserted in the header, and thus electrically connected to the can. The proximal end of the lead, the end that connects to the can, typically includes a conductive metal member that is inserted into a "header" portion of the can. The header is normally constructed of a transparent, biocompatible material and includes a receptacle for receiving the proximal end of the lead. The header's electrical contacts within this receptacle connect to circuitry in the can by one or more wires. In the presence of body fluids present during surgery, it can be difficult for a surgeon to determine whether the lead has been completely inserted into the header. If the lead is not fully inserted into the header, the pacemaker may function erratically or not function at all.

Thus, it would be desirable to develop an implantable medical device, such as a pacemaker, that provides the surgeon a positive indication of proper lead insertion into the device. Such a device would give the surgeon increased confidence that the lead has been effectively mated with the pacemaker. Despite the significant advantages that could be offered by such a device, to date, no such implantable device connection is known to exist.

SUMMARY OF THE INVENTION

Accordingly, there is provided herein an implantable medical device including an enclosure (or "can") with a header component connected thereto. The header includes one or more lead cavities into which a lead can be inserted and conductors connecting the lead to electronics that are contained within the can. The lead cavity includes a retaining device, such as a spring, for retaining a highly visible indicator plunger that is at least partially hidden from view inside the volume defined by an annular electrode, or other opaque object, that partially surrounds the lead cavity. The indicator plunger preferably is hidden from view before the lead is inserted into the header.

When a lead is inserted into the lead cavity, the end of the lead mated with the lead cavity pushes against the indicator plunger, thereby moving the plunger and compressing the spring. When the lead is fully inserted into the lead cavity, the plunger is pushed away from the volume defined by the annular electrode and becomes visible. Thus, the indicator plunger is hidden from view when a lead is not inserted fully into the lead cavity, and becomes visible only when the lead is fully inserted into the lead cavity. In this way, the plunger provides a positive indication that the lead has been fully inserted into the header.

The indicator plunger includes at least a portion that is easily visible to a surgeon during implantation once the lead is fully inserted into the lead cavity. That portion may be identified with a highly visible color such as blue or yellow or otherwise be constructed of a material with high contrast relative to the surrounding header components.

The annular electrode that hides the indicator plunger prior to full lead insertion may also include a retaining "stop" surface that will contact a corresponding flanged surface on the plunger should the plunger break loose from the spring. This feature is designed to prevent the plunger from floating freely out of the lead cavity and into the patient's body should the plunger break away from the spring.

Thus, the present invention comprises a combination of features and advantages that enable it to substantially advance the art by including an indicator that positively indicates complete lead insertion. A surgeon can thereby ensure that a lead is adequately attached to the electronics assembly during implantation.

BRIEF DESCRIPTION OF THE DRAWINGS

A better understanding of the present invention can be obtained when the following detailed description of the preferred embodiments is considered in conjunction with the following drawings, in which.

DETAILED DESCRIPTION OF PREFERRED EMBODIMENTS

Figure 1:
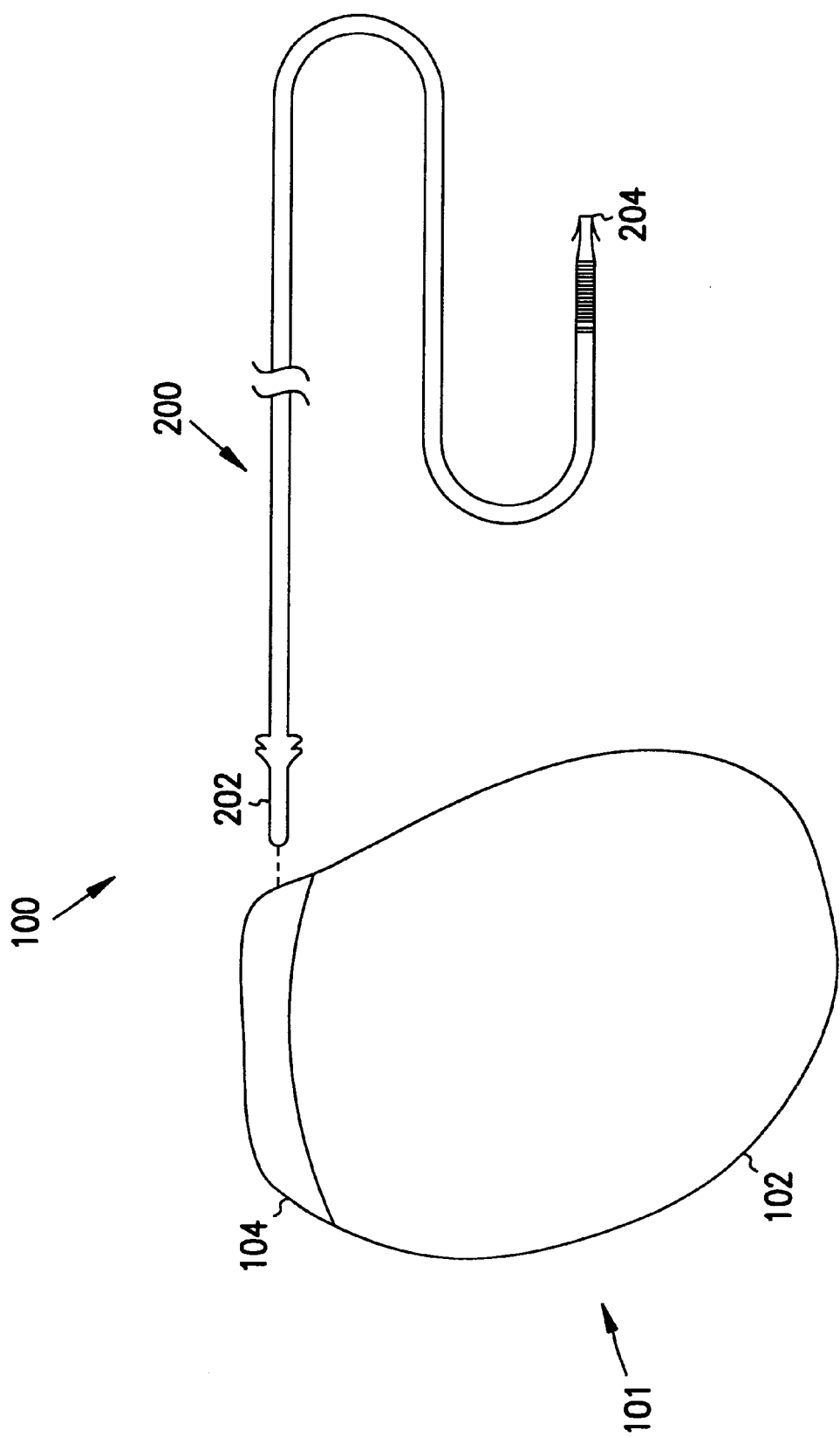
FIG. 1 is a schematic representation of an implantable medical device and a lead constructed in accordance with the preferred embodiment of the invention.

Referring now to FIG. 1, an implantable medical device 100, constructed in accordance with a preferred embodiment of the invention, generally includes an electronics assembly 101 and a lead 200. The implantable medical device 100 depicted is a pacemaker, but the invention may include any medical device that includes two portions that are mated together during implantation. Thus, the principles of the invention apply to a defibrillator, nerve stimulator, and drug delivery device to name a few.

The electronics assembly 101 includes a housing, or "can," 102 and a header 104. The can 102 includes electronic components for processing electrical signals from the heart and for generating pacing pulses to cause the heart to beat. The electronics preferably also includes a microprocessor or other type of control logic for controlling the operation of the pacemaker and selecting a suitable pacing therapy for the patent. An example of a pacemaker's electronics can be found in U.S. Pat. No. 5,411,537, assigned to Sulzer Intermedics.

The can preferably is constructed of titanium or other biocompatible material. The header 104 is constructed of a transparent biocompatible material and is attached to can 102 and includes electrical contacts (not specifically shown in FIG. 1) for receiving lead 200. The header permits an electrical connection between lead 200 and the electronics inside the can. To minimize the potential for body fluids leaking into the can and damaging the electronic components, the can is hermetically sealed. The header preferably is made of epoxy resin or similar thermosetting polymer material that is formed in situ. In addition, other materials may be used, such as polycarbonate urethane. As used in this description and the claims which follow, "transparent" simply means that the contents of the header can be seen. Thus, a transparent header may be clear, colored, or have some visual distortion but permits the components inside the header to be seen.

Referring still to FIG. 1, the lead 200 includes at least one conductor (not shown), and if desired two or more conductors, wrapped by an insulative layer. In the preferred embodiment described herein, lead 200 includes two conductors and thus is referred to as a "bipolar" lead. As shown in FIG. 1, lead 200 includes a proximal end 202 which is inserted into header 104 to couple the lead to the electronics assembly 101 and a distal end 204 which connects to the heart tissue to be stimulated and/or monitored by the pacemaker. If desired, pacemaker 100 may alternatively use two or more leads to stimulate and/or monitor the heart at two or more locations inside the heart. During implantation, the surgeon connects the lead 200 to the header 104. The header 104 includes the mechanism described below that provides a positive indication to the surgeon that the lead has been "adequately inserted" into the header to make sufficient contact with the header. The term "adequate insertion" means that the lead has been inserted sufficiently so as to establish electrical connection with the contacts in the header, while avoiding or minimizing the potential for the pacemaker to function erratically or not function at all. Other terms that are intended to mean the same thing as "adequate insertion" include "full," sufficient," or "complete" lead insertion.

Figure 2:
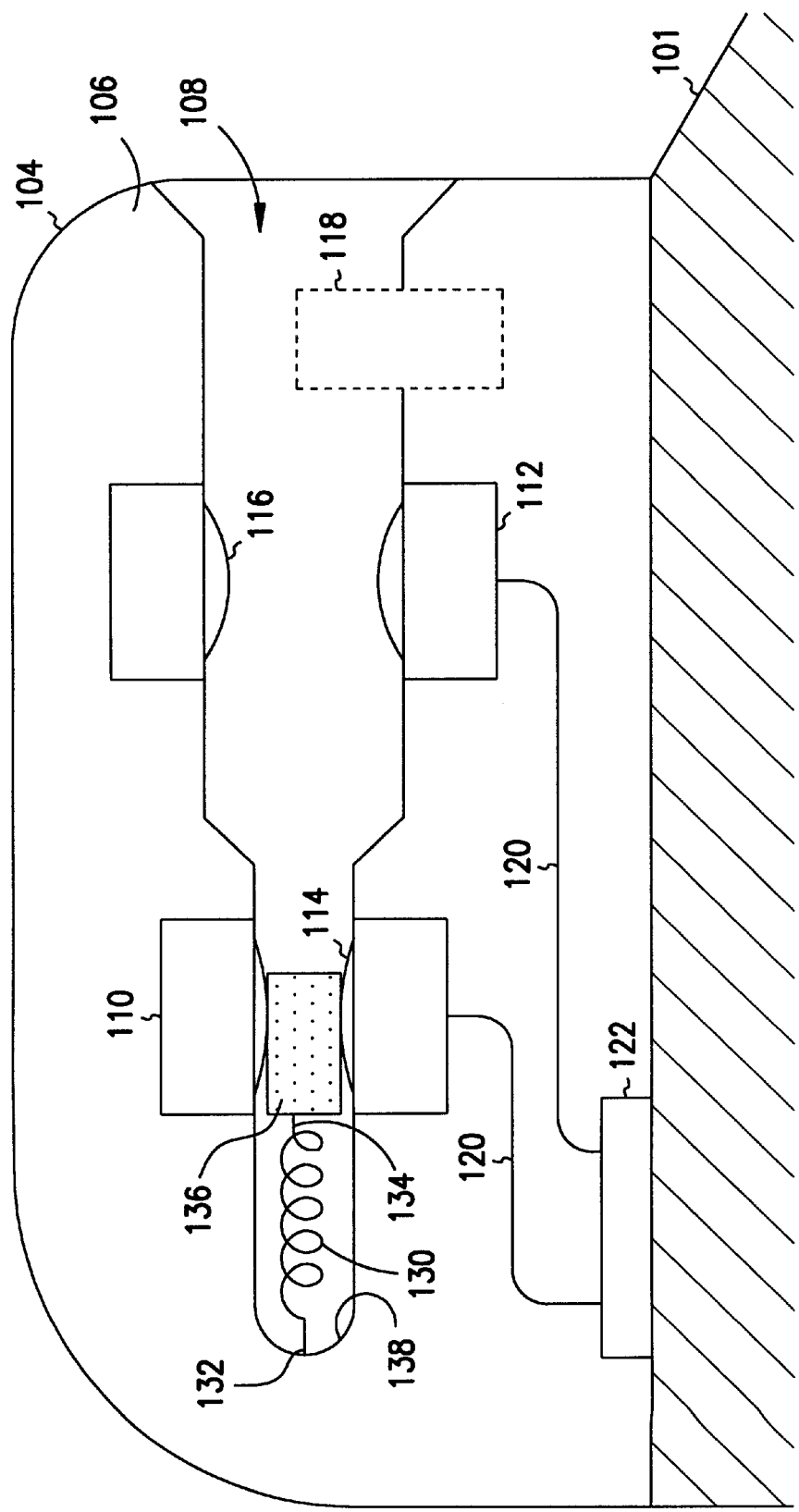
FIG. 2 is an enlarged detailed view of a header portion of the implantable device of FIG. 1 with a positive indicator plunger hidden from view by an annular electrode.
Figure 3:
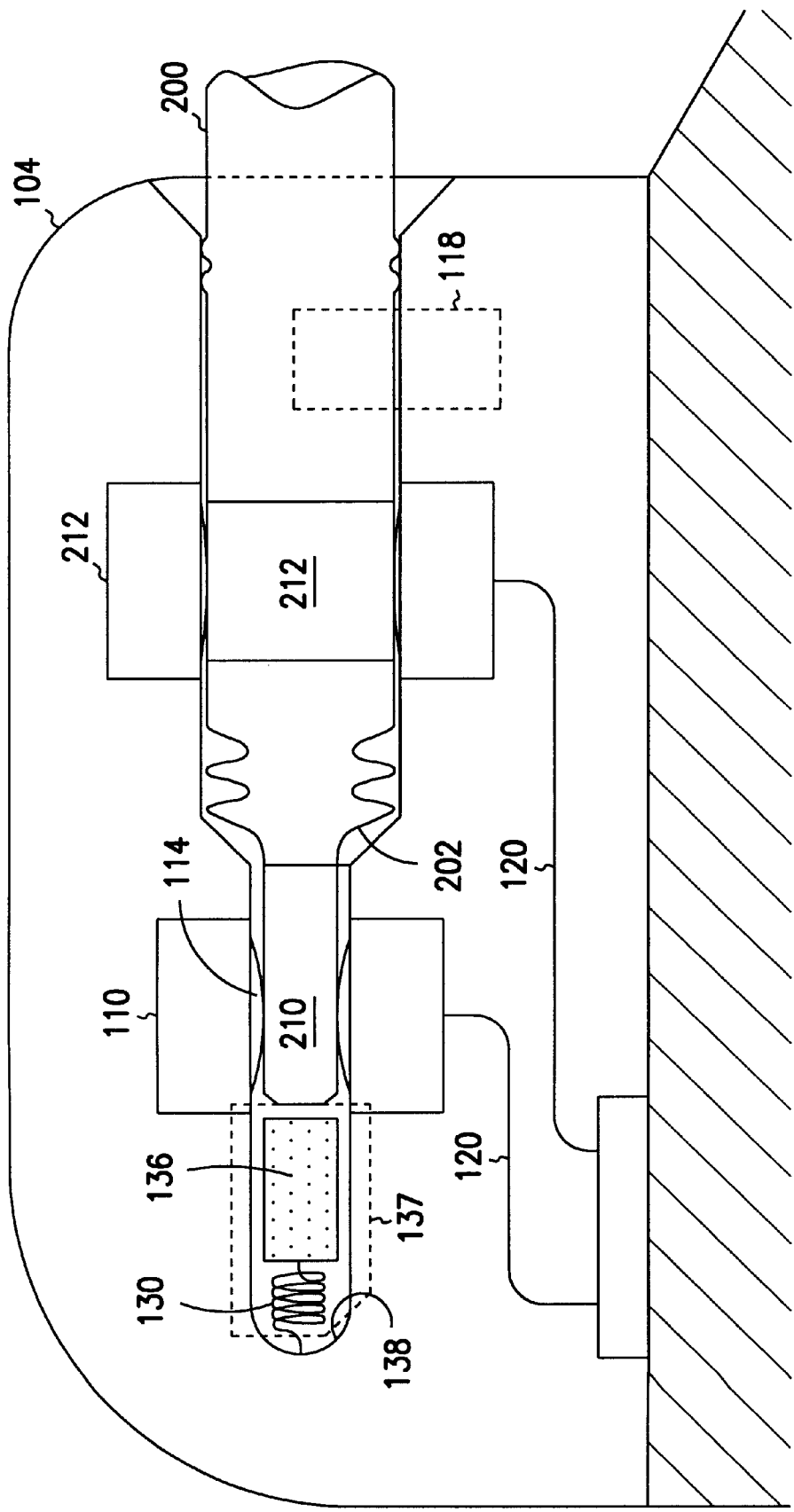
FIG. 3 an enlarged view of the header portion similar to FIG. 2 but having a lead end completely inserted so that the indicator plunger becomes visible through the header.

FIGS. 2 and 3 show the header 104 in greater detail. The header includes a lead cavity 108 formed in, or otherwise constructed from, transparent material 106. The lead cavity 108 preferably comprises the shape shown in FIG. 2 to receive the proximal lead end 202 as shown in FIG. 3. Two annular electrodes 110 and 112 are included within header material 106. The annular electrodes generally surround lead cavity 108 as shown. When the lead is inserted into the header each electrode makes electrical contact with a corresponding electrode on bipolar lead 200 (FIG. 3). Accordingly, lead electrode 210 couples to header electrode 110 and lead electrode 212 couples to header electrode 112. Sufficient electrical contact between the lead's electrodes 210, 212 and the header's electrodes 110, 112 is shown by way of spring loaded electrical contacts 112 and 114. Thus, electrode 110 includes a spring loaded contact 114 and electrode 112 includes a spring loaded contact 116. When the lead 200 is inserted into header 104, the lead's electrodes press against the spring loaded contacts thereby establishing electrical connectivity between header electrodes 110, 112 and lead electrodes 210, 212.

A locking pin 118 may be included, if desired, to help hold the lead 200 matably engaged with the header 104. Once the lead 200 is inserted into the lead cavity, the locking pin 118 is activated by pressing the pin into the header and against the lead. The locking pin is held in place against the lead by friction or other suitable means. Alternatively, one or more set screws could be used to hold lead 200 engaged with header 104.

In accordance with the preferred embodiment, the header 104 includes a mechanism 137 to positively indicate when a lead has been fully inserted into header 104. As shown in FIGS. 2 and 3, this mechanism preferably includes a spring 130 and a positive indicator plunger 136. One end 132 of the spring 130 connects to the rear surface 138 of the lead cavity 108. The other end 134 of the spring connects to the indicator plunger 136. When no lead has been inserted into the header, the plunger is pushed away from the rear surface 138 of the lead cavity by the natural tendency of the spring. Thus, the position of the plunger in FIG. 2 represents the plunger's normal resting position as determined by the length of the spring with no compressive or tensive forces applied. The plunger preferably is hidden from view through the header by the annular, opaque electrode 110. Alternatively, any other opaque object besides electrode 110 can be incorporated into header 104 to hide the indicator plunger in its normal resting position.

In FIG. 3, however, a lead 200 is shown disposed within the lead cavity. The proximal end 202 of the lead presses against the plunger and pushes the plunger toward the rear surface 138 of the lead cavity. Insertion of the lead end 202 compresses spring 130 and the plunger is pushed generally into the rear portion of the lead cavity. In this location, the plunger becomes highly visible to the surgeon through the transparent header 104 thereby indicating that the lead has been fully inserted into the header. Preferably, the plunger is suitably marked to make the plunger easily visible through the header. Accordingly, the visual properties of the plunger, such as color, and brilliance, may be selected to emphasize the contrast between the indicator plunger and the other components of the header and can. A suitable material for constructing the plunger is titanium that has been treated to exhibit a highly visible surface coloration, such as blue or yellow. Alternatively, the plunger may be incorporated with beads of glass, plastic or ceramic that have a distinct coloration. In sum, the indicator plunger is constructed and marked so that the plunger becomes easily visible to a surgeon during implantation once the lead is adequately inserted.

The spring 130 used to retain the plunger in the rear portion of the lead cavity preferably has a spring constant of 10 to 30 grams. The spring preferably is constructed from titanium or other suitable material. Further, it is contemplated that other types of devices or mechanisms, rather than a spring, may be used. Any flexible material, such as silicone, can be used which has a natural length sufficient to keep plunger 136 hidden from view before a lead is inserted into the lead cavity and which can be compressed upon insertion of the lead.

Thus, the preferred embodiment of header 104 includes an indicator plunger that normally is hidden from view. The plunger becomes visible only once a lead has been fully and completely inserted into the header. If the surgeon has inserted the lead, but the plunger is not visible, the surgeon will then know that the lead has not been adequately inserted into the header of the pacemaker.

Figure 4:
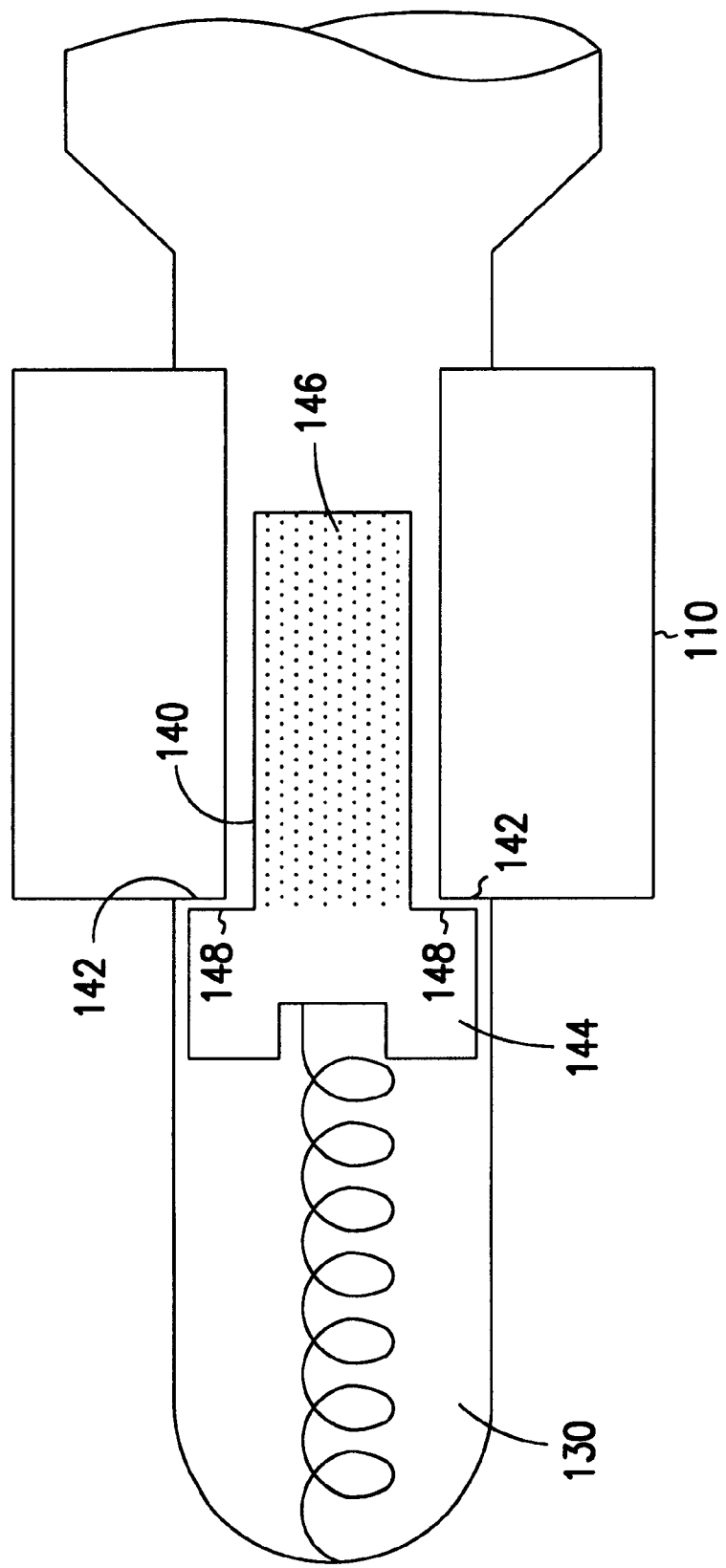
FIG. 4 is an alternative embodiment of the plunger of FIGS. 2 and 3.

Numerous alternative embodiments are contemplated for the positive lead insertion indicator plunger 130 shown in FIGS. 2 and 3. For example, to provide additional safeguards to retain the plunger within the header should the indicator plunger break loose from the spring 130, which normally retains the plunger hidden from view, the alternative embodiment shown in FIG. 4 could be used to prevent the plunger from exiting the header into the patient's body. Although this problem is not likely to occur, if it was to occur it might occur when the can is implanted and before the lead is connected to the header, or when the lead or can malfunctions or wears out and has to be replaced in subsequent surgery. As shown in FIG. 4, the indicator plunger 140 includes a flanged vertical surface 148 forming a stop. Preferably, the annular electrode 110 includes a stop surface 142 that protrudes into the lead cavity. The flanged surface 148 of the indicator plunger 140 may contact surface 142 of electrode 110 preventing the plunger from exiting the header. Thus, if the plunger 140 accidentally breaks loose from spring 130, the surface 142 of electrode 110 restrains the plunger in the rear compartment of the header.

As shown in FIG. 4, not all of the indicator plunger 140 may be marked in a contrasting manner for high visibility. For example, the end portion 144 of the plunger that connects to the spring may not be marked for high visibility, while plunger end portion 146 normally hidden from view by annular electrode 110 is marked for high visibility. Alternatively, end portions 144 and 146 may be marked for high visibility in different ways so that a surgeon can easily ascertain whether end portion 146 is visible once a lead is inserted into the header.

Numerous variations and modifications will become apparent to those skilled in the art once the above disclosure is fully appreciated. It is intended that the following claims be interpreted to embrace all such variations and modifications.

What is claimed:

1. An implantable medical device, comprising:
   a housing containing electronic components; and
   a header mated with said housing and adapted to receive a lead, said header including a movable indicator to positively indicate when a lead has been fully inserted into said header.

2. The implantable device of claim 1, wherein said header is transparent.

3. The implantable device of claim 2 wherein said indicator includes a plunger that is moved when a lead is inserted into said header.

4. The implantable device of claim 2 wherein said indicator includes a spring connected to a plunger.

5. The implantable device of claim 4 wherein said spring becomes compressed when a lead is inserted into said header.

6. The implantable device of claim 2 wherein said indicator includes a plunger and a spring that maintains said plunger hidden from view and compresses when a lead is inserted and when the lead is fully inserted permits said plunger to be visible through said header.

7. The implantable device of claim 2 wherein said indicator is colored differently from the other visible portions of said implantable device.

8. An implantable medical device, comprising:
   a housing;
   a header attached to said housing and adapted to receive a lead, said header including an indicator adapted to provide a positive indication that a lead has been fully inserted in said header, said indicator comprising:
   a retaining device; and
   an indicator plunger substantially hidden from view when no lead is disposed within said header.

9. The implantable device of claim 8 wherein said indicator plunger is movable by a lead inserted into said header.

10. The implantable device of claim 8 wherein said plunger includes a first surface against which an end of a lead pushes as the lead is inserted into said header.

11. The implantable device of claim 8 wherein said header includes a lead cavity into which a lead can be inserted and said retaining device is connected to a surface defining said lead cavity and said retaining device also connects to said indicator plunger.

12. The implantable device of claim 11 further including a substantially annular electrode surrounding a portion of said lead cavity.

13. The implantable device of claim 12 wherein said indicator plunger is substantially hidden from view by said annular electrode when no lead is inserted into said header.

14. The implantable device of claim 13 wherein said indicator plunger includes a surface against which a lead pushes as the lead is inserted into said lead cavity.

15. The implantable device of claim 14 where said indicator plunger is moved to a position outside said annular electrode when a lead is fully inserted into said lead cavity so that said plunger becomes viewable.

16. The implantable device of claim 8 wherein said retaining device comprises a spring.

17. The implantable device of claim 12 wherein said retaining device holds a portion of said plunger in place within the volume defined by the annular electrode.

18. The implantable device of claim 17 wherein said annular electrode includes a retaining surface for preventing said plunger from exiting said lead cavity.

19. An implantable medical device, comprising:
   a lead for connection to human tissue;
   a housing containing electronics;
   a header coupled to said housing, said header comprising transparent material defining a lead cavity and including:
   a spring connected to an end portion of said lead cavity;
   an indicator plunger connected to said spring and at least partially hidden from view by an opaque portion of said header when no lead is fully inserted into said lead cavity;
   wherein said plunger is pushed away from the position in which the plunger is at least partially hidden to a position in which the plunger is viewable through the header when a lead is fully inserted into said lead cavity.

20. The implantable device of claim 19 wherein said plunger has a coloration that is different than the rest of the header.

21. A cardiac stimulator, comprising:

a can;

a transparent header hermetically-sealed to said can and adapted to receive a cardiac lead, said header including a positive indicator device that has a high contrast portion hidden from view through the header by an opaque component and said high contrast portion becomes viewable through the header when a lead is completely inserted into said header.

22. An implantable medical device, comprising:

a housing containing electronic components; and a header mated with the housing and adapted to receive a lead, the header is transparent, the header including an indicator to positively indicate when the lead has been fully inserted into the header, the indicator includes a plunger that is moved when the lead is inserted into the header.

23. An implantable medical device, comprising:

a housing containing electronic components; and a header mated with the housing and adapted to receive a lead, the header is transparent, the header including an indicator to positively indicate when the lead has been fully inserted into the header, the indicator including a spring connected to a plunger.

24. The implantable device of claim 23 wherein the spring becomes compressed when the lead is inserted into the header.

25. An implantable medical device, comprising:

a housing containing electronic components; and a header mated with the housing and adapted to receive a lead, the header is transparent, the header including an indicator to positively indicate when the lead has been fully inserted into the header, the indicator including a plunger and a spring that maintains the plunger hidden from view and compresses when the lead is inserted and when the lead is fully inserted permits the plunger to be visible through the header.

* * * * *